United States Patent [19]
Watson et al.

[11] Patent Number: 5,833,929
[45] Date of Patent: Nov. 10, 1998

[54] AUTOMATIC AIR FRESHENER AND DEODORIZER

[76] Inventors: Ernest Watson; Carlton Watson, both of 3704 Briar La., Hazel Crest, Ill. 60429

[21] Appl. No.: 936,949

[22] Filed: Sep. 25, 1997

[51] Int. Cl.⁶ .................................................. A62B 7/08
[52] U.S. Cl. .................................................. 422/123; 454/157
[58] Field of Search ........................... 34/576, 579, 582, 34/585, 60, 61; 454/75, 157, 337; 222/644, 645, 646; 422/123, 124

[56] References Cited

U.S. PATENT DOCUMENTS

| | | | |
|---|---|---|---|
| 2,882,809 | 4/1959 | Nelson | 454/144 |
| 3,259,050 | 7/1966 | Grimm III | 454/157 |
| 4,913,034 | 4/1990 | Ripple et al. | 454/157 |
| 5,078,046 | 1/1992 | Mascolo et al. | 454/157 |
| 5,171,485 | 12/1992 | Ryan | 422/124 X |
| 5,297,988 | 3/1994 | Nishino et al. | 422/124 X |

FOREIGN PATENT DOCUMENTS 27 28 393  1/1979  Germany.

*Primary Examiner*—Henry A. Bennett
*Assistant Examiner*—Steve Gravini

[57] ABSTRACT

A new automatic air freshener and deoderizer for releasing a scent into an interior of a vehicle. The inventive device includes a pump disposed within a housing. The housing is positioned within a trunk of a vehicle. The pump has wiring extending outwardly therefrom. The housing has an opening extending within a top wall thereof. The opening is in communication with the pump. The opening receives an air fragrance canister therein. The air fragrance canister has an outlet pipe connected to an inlet tube of the pump. The pump has an outlet tube directed outwardly of the housing. A tube extends outwardly of the outlet tube of the pump. The tube extends into a bifurcated outer portion with open ends. The bifurcated outer portion is positionable beneath seats of the vehicle. Each of the open ends have a dispensing nozzle disposed thereon. A power switch is secured to a dashboard of the vehicle. The power switch is in communication with a battery of the vehicle. The power switch couples with the wiring of the pump.

1 Claim, 2 Drawing Sheets

AUTOMATIC AIR FRESHENER AND DEODORIZER

BACKGROUND OF THE INVENTION

1. Field of the Invention

The present invention relates to air fresheners and more particularly pertains to a new automatic air freshener and deoderizer for releasing a scent into an interior of a vehicle.

2. Description of the Prior Art

The use of air fresheners is known in the prior art. More specifically, air fresheners heretofore devised and utilized are known to consist basically of familiar, expected and obvious structural configurations, notwithstanding the myriad of designs encompassed by the crowded prior art which have been developed for the fulfillment of countless objectives and requirements.

Known prior art air fresheners include U.S. Pat. No. 5,171,485 to Ryan; U.S. Pat. No. 4,722,264 to DeGuisseppe; U.S. Pat. No. Des. 280,014 to Tanaka; U.S. Pat. No. 5,297,988 to Nishino et al.; U.S. Pat. No. 4,814,212 to Spector; and U.S. Pat. No. 4,200,229 to Spector.

While these devices fulfill their respective, particular objectives and requirements, the aforementioned patents do not disclose a new automatic air freshener and deoderizer. The inventive device includes a pump disposed within a housing. The housing is positioned within a trunk of a vehicle. The pump has wiring extending outwardly therefrom. The housing has an opening extending within a top wall thereof. The opening is in communication with the pump. The opening receives an air fragrance canister therein. The air fragrance canister has an outlet pipe connected to an inlet tube of the pump. The pump has an outlet tube directed outwardly of the housing. A tube extends outwardly of the outlet tube of the pump. The tube extends into a bifurcated outer portion with open ends. The bifurcated outer portion is positionable beneath seats of the vehicle. Each of the open ends have a dispensing nozzle disposed thereon. A power switch is secured to a dashboard of the vehicle. The power switch is in communication with a battery of the vehicle. The power switch couples with the wiring of the pump.

In these respects, the automatic air freshener and deoderizer according to the present invention substantially departs from the conventional concepts and designs of the prior art, and in so doing provides an apparatus primarily developed for the purpose of releasing a scent into an interior of a vehicle.

SUMMARY OF THE INVENTION

In view of the foregoing disadvantages inherent in the known types of air fresheners now present in the prior art, the present invention provides a new automatic air freshener and deoderizer construction wherein the same can be utilized for releasing a scent into an interior of a vehicle.

The general purpose of the present invention, which will be described subsequently in greater detail, is to provide a new automatic air freshener and deoderizer apparatus and method which has many of the advantages of the air fresheners mentioned heretofore and many novel features that result in a new automatic air freshener and deoderizer which is not anticipated, rendered obvious, suggested, or even implied by any of the prior art air fresheners, either alone or in any combination thereof.

To attain this, the present invention generally comprises a pump disposed within a housing. The housing is positioned within a trunk of a vehicle. The pump has wiring extending outwardly therefrom. The housing has an opening extending within a top wall thereof. The opening is in communication with the pump. The opening receives an air fragrance canister therein. The air fragrance canister has an outlet pipe connected to an inlet tube of the pump. The pump has an outlet tube directed outwardly of the housing. A tube extends outwardly of the outlet tube of the pump. The tube extends into a bifurcated outer portion with open ends. The bifurcated outer portion is positionable beneath seats of the vehicle. Each of the open ends have a dispensing nozzle disposed thereon. A power switch is secured to a dashboard of the vehicle. The power switch is in communication with a battery of the vehicle. The power switch couples with the wiring of the pump.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended thereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new automatic air freshener and deoderizer apparatus and method which has many of the advantages of the air fresheners mentioned heretofore and many novel features that result in a new automatic air freshener and deoderizer which is not anticipated, rendered obvious, suggested, or even implied by any of the prior art air fresheners, either alone or in any combination thereof.

It is another object of the present invention to provide a new automatic air freshener and deoderizer which may be easily and efficiently manufactured and marketed.

It is a further object of the present invention to provide a new automatic air freshener and deoderizer which is of a durable and reliable construction.

An even further object of the present invention is to provide a new automatic air freshener and deoderizer which is susceptible of a low cost of manufacture with regard to both materials and labor, and which accordingly is then susceptible of low prices of sale to the consuming public, thereby making such automatic air freshener and deoderizer economically available to the buying public.

Still yet another object of the present invention is to provide a new automatic air freshener and deoderizer which provides in the apparatuses and methods of the prior art some of the advantages thereof, while simultaneously overcoming some of the disadvantages normally associated therewith.

Still another object of the present invention is to provide a new automatic air freshener and deoderizer for releasing a scent into an interior of a vehicle.

Yet another object of the present invention is to provide a new automatic air freshener and deoderizer which includes a pump disposed within a housing. The housing is positioned within a trunk of a vehicle. The pump has wiring extending outwardly therefrom. The housing has an opening extending within a top wall thereof. The opening is in communication with the pump. The opening receives an air fragrance canister therein. The air fragrance canister has an outlet pipe connected to an inlet tube of the pump. The pump has an outlet tube directed outwardly of the housing. A tube extends outwardly of the outlet tube of the pump. The tube extends into a bifurcated outer portion with open ends. The bifurcated outer portion is positionable beneath seats of the vehicle. Each of the open ends have a dispensing nozzle disposed thereon. A power switch is secured to a dashboard of the vehicle. The power switch is in communication with a battery of the vehicle. The power switch couples with the wiring of the pump.

Still yet another object of the present invention is to provide a new automatic air freshener and deoderizer that fulfills the need for a permanently installed fragrance dispensing system for motor vehicle interiors.

Even still another object of the present invention is to provide a new automatic air freshener and deoderizer that could be installed in aftermarket vehicles as well as incorporated into new vehicle production.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
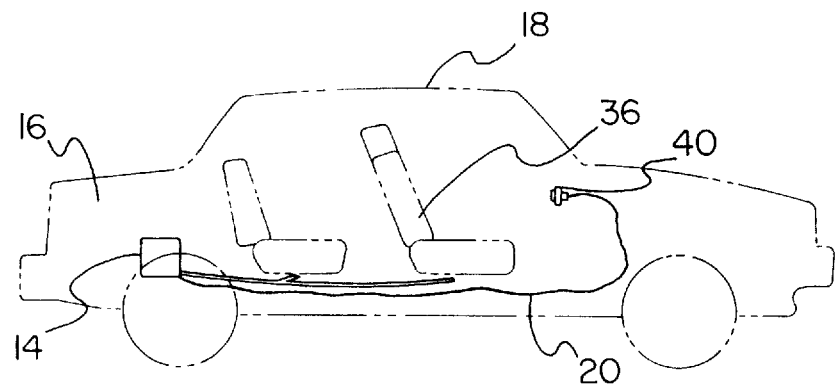
FIG. 1 is a side view of a new automatic air freshener and deoderizer according to the present invention shown installed within a vehicle.
Figure 2:
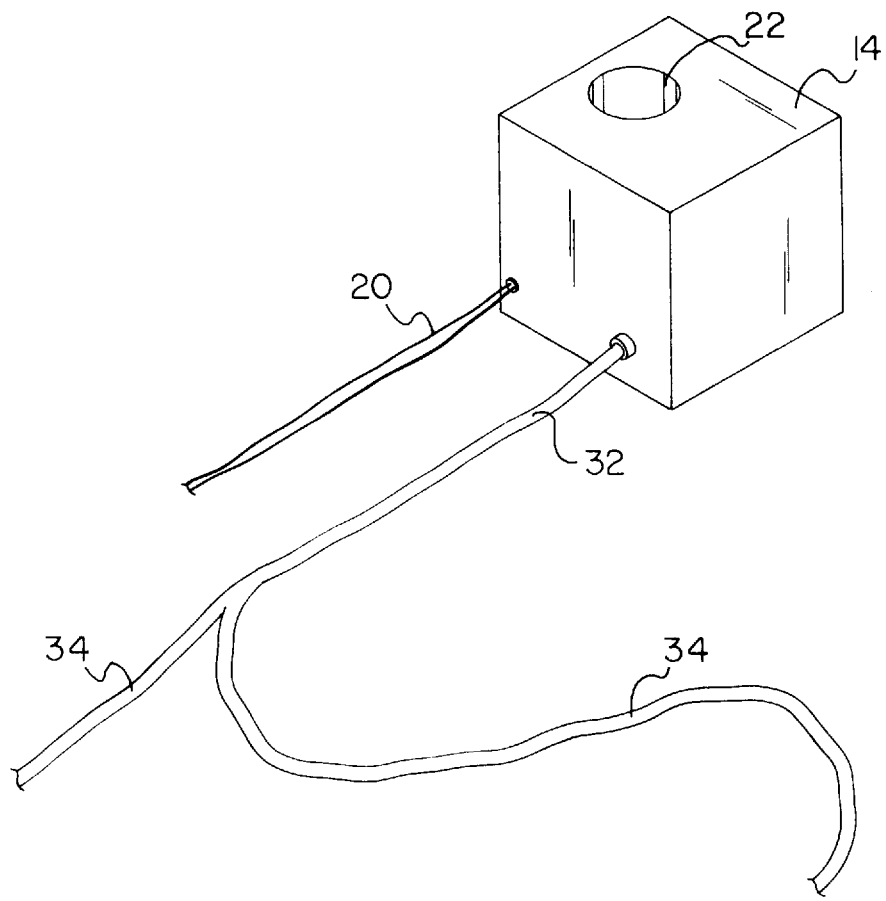
FIG. 2 is a perspective view of the pump of the present invention.
Figure 3:
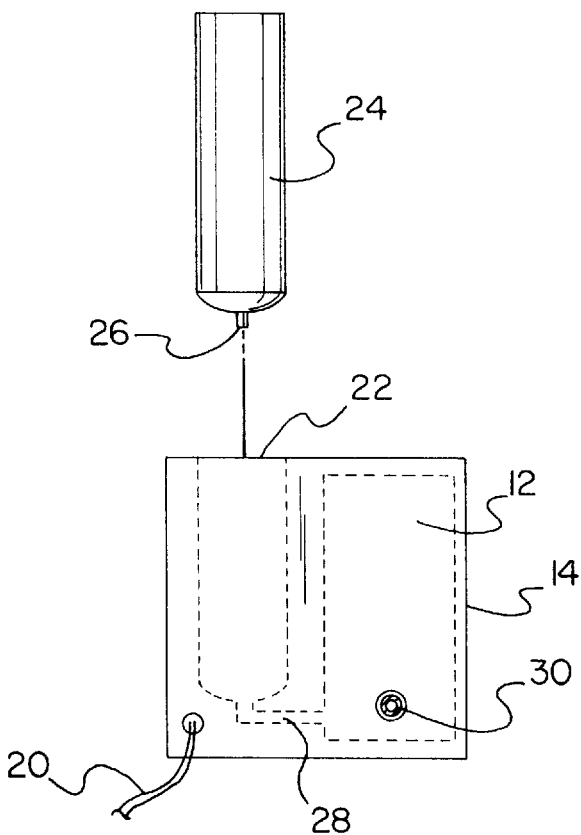
FIG. 3 is a side view of the pump and canister of the present invention.
Figure 4:
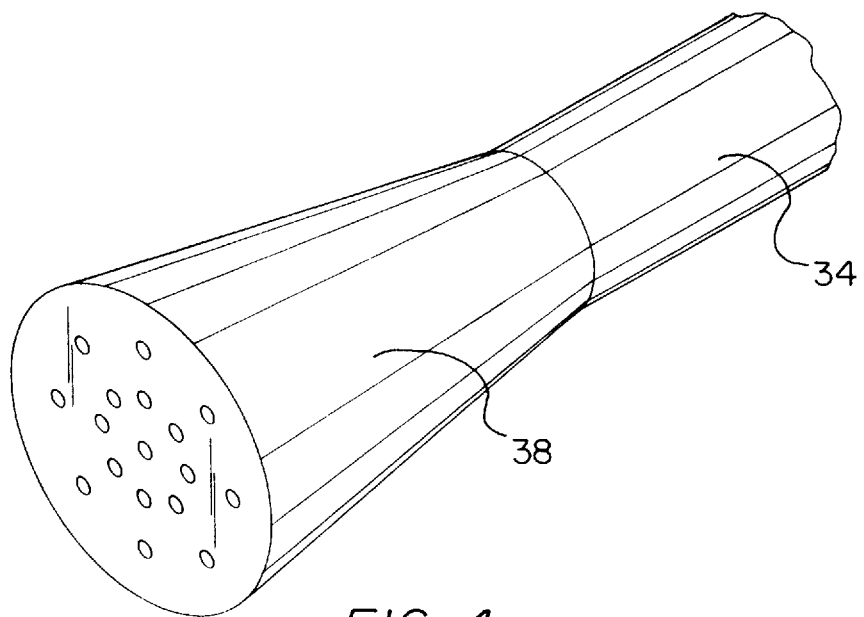
FIG. 4 is a perspective view of one of the dispensing nozzles of the present invention.

With reference now to the drawings, and in particular to FIGS. 1 through 4 thereof, a new automatic air freshener and deoderizer embodying the principles and concepts of the present invention and generally designated by the reference numeral 10 will be described.

As best illustrated in FIGS. 1 through 4, the automatic air freshener and deoderizer 10 comprises a pump 12 disposed within a housing 14. The housing 14 is positioned within a trunk 16 of a vehicle 18. The pump 12 has wiring 20 extending outwardly therefrom. The housing 14 has an opening 22 extending within a top wall thereof. The opening 22 is in communication with the pump 12. The opening 22 receives an air fragrance canister 24 therein. The air fragrance canister 24 has an outlet pipe 26 connected to an inlet tube 28 of the pump 12. The pump 12 has an outlet tube 30 directed outwardly of the housing 14.

A tube 32 extends outwardly of the outlet tube 30 of the pump 12. The tube 32 extends into a bifurcated outer portion 34 with open ends. The bifurcated outer portion 34 is positionable beneath seats 36 of the vehicle 18. Each of the open ends have a dispensing nozzle 38 disposed thereon.

A power switch 40 is secured to a dashboard of the vehicle 18. The power switch 40 is in communication with a battery of the vehicle 18. The power switch 40 couples with the wiring 20 of the pump 12.

In use, when a motorist wants to improve the smell of the interior, the power switch 40 would be pushed to energize the small electric pump 12 within the trunk 16. Scented fluid would be extracted from the fragrance canister 24 and forced through the tubes 34 to be atomized at the mist nozzles 38 under the seats 36. This would quickly improve the aroma within the vehicle 18. As long as the power switch 40 or button is pushed, the scented mist would be released. Once the fragrance canister 24 eventually runs dry, it could be removed from the housing 14 and a new canister 24 inserted into its place.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A new automatic air freshener and deoderizer for releasing a scent into an interior of a vehicle comprising, in combination:

a pump disposed within a housing, the housing positioned within a trunk of a vehicle, the pump having wiring extending outwardly therefrom, the housing having an opening extending within a top wall thereof, the opening being in communication with the pump, the opening receiving an air fragrance canister therein, the air fragrance canister having an outlet pipe connected to an inlet tube of the pump, the pump having an outlet tube directed outwardly of the housing;

a tube extending outwardly of the outlet tube of the pump, the tube extending into a bifurcated outer portion with open ends, the bifurcated outer portion positionable beneath seats of the vehicle, each of the open ends having a dispensing nozzle disposed thereon; and a power switch secured to a dashboard of the vehicle, the power switch being in communication with a battery of the vehicle, the power switch coupling with the wiring of the pump.

* * * * *